United States Patent
Hwang et al.

(10) Patent No.: US 10,493,268 B2
(45) Date of Patent: Dec. 3, 2019

(54) APPARATUS FOR INVASIVE INSERTION OF ELECTRODE STRUCTURE

(71) Applicant: KOREA INSTITUTE OF SCIENCE AND TECHNOLOGY, Seoul (KR)

(72) Inventors: Donghyun Hwang, Seoul (KR); Keehoon Kim, Seoul (KR); Sang Rok Oh, Gangneung-si (KR); Sehyuk Yim, Seoul (KR); Yong Seok Ihn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 220 days.

(21) Appl. No.: 15/678,894

(22) Filed: Aug. 16, 2017

(65) Prior Publication Data
US 2018/0104478 A1    Apr. 19, 2018

(30) Foreign Application Priority Data
Oct. 18, 2016  (KR) .................. 10-2016-0135194

(51) Int. Cl.
| | |
|---|---|
| *A61N 1/05* | (2006.01) |
| *A61B 18/00* | (2006.01) |
| *A61B 18/14* | (2006.01) |
| *A61N 1/06* | (2006.01) |

(52) U.S. Cl.
CPC .... *A61N 1/0551* (2013.01); *A61B 2018/0019* (2013.01); *A61B 2018/1495* (2013.01); *A61N 1/0529* (2013.01); *A61N 1/06* (2013.01)

(58) Field of Classification Search
CPC ............ A61B 18/14; A61B 2018/0019; A61B 2018/1495; A61B 17/3468; A61B 17/1617; A61B 17/1697; A61B 2017/00566; A61B 2018/00434; A61B 2018/00446; A61B 5/04001; A61B 5/0051; A61B 2017/00398; A61B 2017/00402; A61B 5/0055; A61N 1/0551; A61N 1/0529; A61N 1/06; A61N 1/0539
See application file for complete search history.

(56) References Cited

U.S. PATENT DOCUMENTS

| | | | | |
|---|---|---|---|---|
| 5,361,760 | A * | 11/1994 | Normann | A61B 5/04001 600/377 |
| 6,304,785 | B1 * | 10/2001 | McCreery | A61N 1/0541 128/899 |
| 7,063,708 | B2 * | 6/2006 | Gibson | A61B 17/3468 606/108 |

(Continued)

FOREIGN PATENT DOCUMENTS

| | | |
|---|---|---|
| KR | 10-0896750 B1 | 5/2009 |
| KR | 10-1159134 B1 | 6/2012 |
| KR | 10-1465163 B1 | 11/2014 |

*Primary Examiner* — Katrina M Stransky
(74) *Attorney, Agent, or Firm* — Birch, Stewart, Kolasch & Birch, LLP

(57) ABSTRACT

An electrode structure inserting apparatus includes an electrode structure fixing unit to which the electrode structure is detachably fixed, and a vibration generator connected to the electrode structure fixing unit to vibrate the electrode structure fixing unit in an insertion direction of the electrode structure, and the electrode structure inserting apparatus inserts the invasive electrode structure into a nerve in a biological tissue.

14 Claims, 10 Drawing Sheets

(56) References Cited

U.S. PATENT DOCUMENTS

| | | | | |
|---|---|---|---|---|
| 7,141,914 B2* | 11/2006 | Kallio | ............... | B25J 7/00 |
| | | | | 310/323.17 |
| 8,226,661 B2 | 7/2012 | Balling et al. | | |
| 8,435,250 B2* | 5/2013 | Yoon | ............... | A61N 1/0529 |
| | | | | 310/323.06 |
| 2007/0296310 A1* | 12/2007 | Kim | ............... | A61B 5/04001 |
| | | | | 310/338 |
| 2010/0168759 A1* | 7/2010 | Yoon | ............... | A61N 1/0529 |
| | | | | 606/129 |
| 2013/0325038 A1* | 12/2013 | Sato | ............... | A61B 17/11 |
| | | | | 606/139 |
| 2014/0012284 A1* | 1/2014 | Sheth | ............... | A61N 1/0539 |
| | | | | 606/129 |
| 2015/0119897 A1* | 4/2015 | Smith | ............... | A61B 17/30 |
| | | | | 606/129 |

\* cited by examiner

APPARATUS FOR INVASIVE INSERTION OF ELECTRODE STRUCTURE

CROSS-REFERENCE TO RELATED APPLICATION

This application claims priority to Korean Patent Application No. 10-2016-0135194, filed on Oct. 18, 2016, and all the benefits accruing therefrom under 35 U.S.C. § 119, the contents of which in its entirety are herein incorporated by reference.

BACKGROUND

1. Field

The present disclosure relates to an apparatus for invasive insertion of an electrode structure.

[Description about National Research and Development Support]

This study was supported by Advanced Convergence Technology Development Project of National Research Foundation of Korea (Project Name: Development of bio-signal measurement and analysis system for movement and tactile transmission, and bionic arm with bio-signal-based control function, Project No. 1711029047) under the superintendence of Ministry of Science, ICT and Future Planning, Republic of Korea.

2. Description of the Related Art

For the insertion of an invasive nerve electrode, in the existing technique, an operating surgeon directly pushes the electrode into a nerve, or the electrode is stricken into the nerve by pneumatic impacts.

When an operating surgeon directly pushes an electrode into a nerve by hand, the operating surgeon may apply an excessive force to penetrate an epineurium of the nerve with the electrode. This may damage the nerve. In addition, since the electrode may have different insertion states depending on the skill of the operating surgeon, it is not easy to ensure sufficient reproduction and iteration of insertion.

When an electrode is stricken into a nerve by pneumatic impacts, generally, a plurality of electrodes are inserted into a brain nerve, but the nerve or electrode may be damaged due to instant impacts. Thus, for accurate insertion, sufficient practices are demanded, and it is difficult for an operating surgeon to directly grip and conveniently use the electrode.

Thus, there is demanded an electrode structure inserting apparatus, which allows an electrode to be accurately inserted just with a simple motion and also minimizes the damage of the nerve and the electrode.

RELATED LITERATURES

Patent Literature

U.S. Pat. No. 8,226,661 (Jul. 24, 2012)

SUMMARY

The present disclosure is directed to providing an electrode structure inserting apparatus which may fix a nerve by a negative pressure and insert an electrode into the nerve while vibrating the electrode which is to be inserted into the nerve.

The object of the present disclosure is not limited to the above, and other objects not mentioned herein will be clearly understood by those skilled in the art from the following description.

In one aspect of the present disclosure, there is provided an electrode structure inserting apparatus for inserting an electrode structure into a nerve in a biological tissue, the apparatus comprising: an electrode structure fixing unit to which the electrode structure is detachably fixed; and a vibration generator connected to the electrode structure fixing unit to vibrate the electrode structure fixing unit in an insertion direction of the electrode structure.

According to an embodiment of the present disclosure, the electrode structure inserting apparatus may further comprise a linear driving unit configured to move the electrode structure fixing unit in the insertion direction.

According to an embodiment of the present disclosure, the electrode structure inserting apparatus may further comprise a nerve fixing unit provided at an insertion end of the electrode structure fixed to the electrode structure fixing unit to suck and fix an insertion portion of the nerve into which the electrode structure is to be inserted.

According to an embodiment of the present disclosure, the electrode structure inserting apparatus may further comprise a flexible connector disposed between the electrode structure fixing unit and the vibration generator to connect the electrode structure fixing unit and the vibration generator.

According to an embodiment of the present disclosure, the flexible connector may have a side groove circumferentially formed at a side of an end thereof to which the vibration generator is connected.

According to an embodiment of the present disclosure, the electrode structure inserting apparatus may further comprise an elastic plate having a through hole in which the electrode structure fixing unit is inserted and fixed, the elastic plate being elastically deformable in the insertion direction.

According to an embodiment of the present disclosure, two or more elastic plates may be arranged in parallel in the insertion direction.

According to an embodiment of the present disclosure, the vibration generator may include a piezoelectric actuator.

According to an embodiment of the present disclosure, the electrode structure inserting apparatus may further comprise an elastic member configured to apply a restoration force to the electrode structure fixing unit which is moved in the insertion direction.

According to an embodiment of the present disclosure, the linear driving unit may include a shape memory alloy wire for moving the electrode structure fixing unit in the insertion direction.

According to an embodiment of the present disclosure, the electrode structure inserting apparatus may further comprise a guide body to which the vibration generator is connected to be slidable in the insertion direction.

According to an embodiment of the present disclosure, the nerve fixing unit may have a nerve fixing groove formed concavely so that the insertion portion of the nerve is placed therein.

According to an embodiment of the present disclosure, the nerve fixing unit may include a suction body in which the electrode structure fixing unit and the vibration generator are disposed, and the suction body may have an electrode structure discharge hole through which the electrode structure passes and a suction hole formed around the electrode structure discharge hole to suck in the insertion portion of the nerve.

DETAILED DESCRIPTION

Hereinafter, an apparatus for insertion of an electrode structure (hereinafter, also referred to as an electrode structure inserting apparatus) according to an embodiment of the present disclosure will be described with reference to the accompanying drawings.

Figure 1:
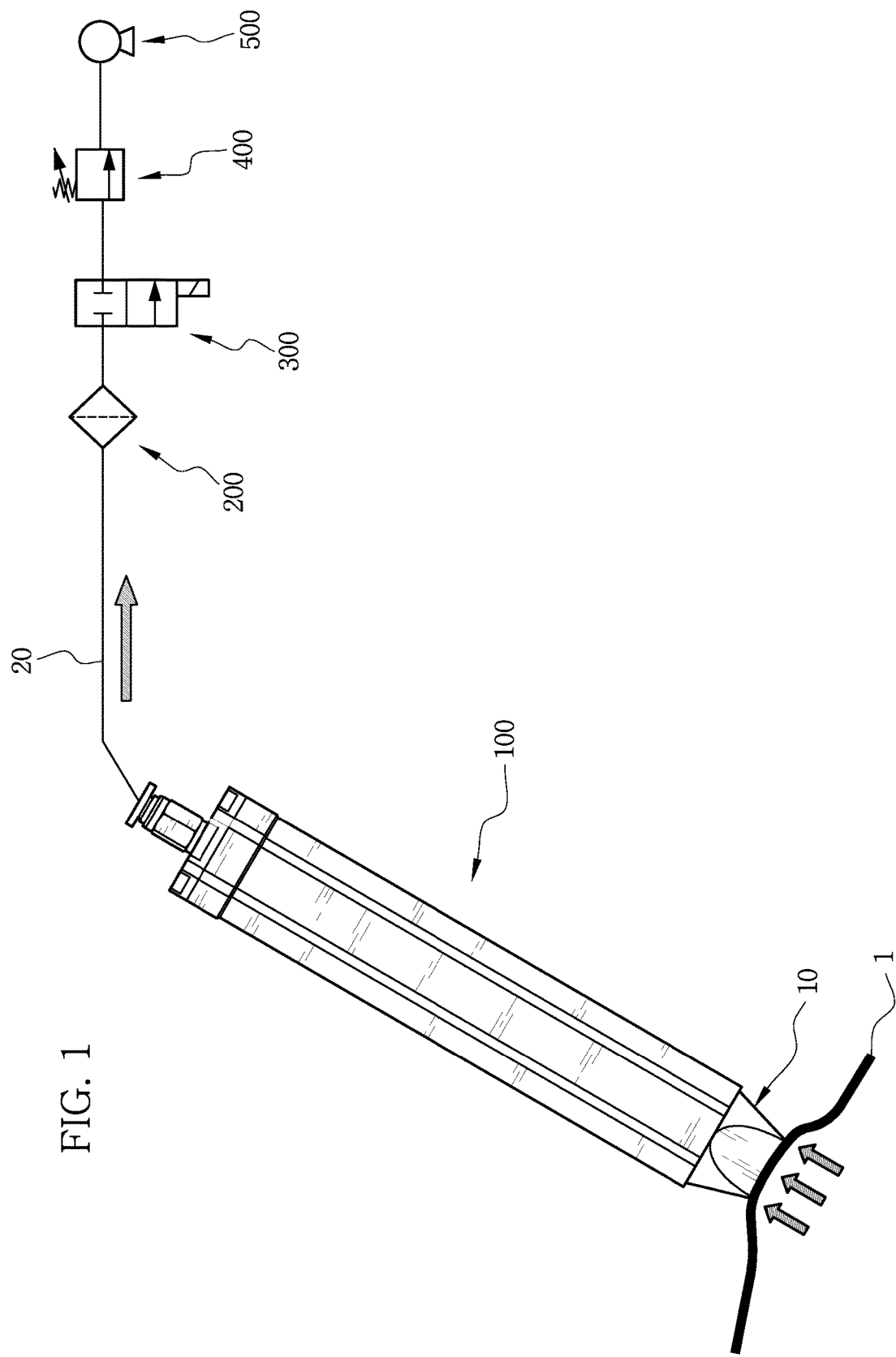
FIG. 1 is a diagram showing an exemplary connection between an electrode structure inserting apparatus according to an embodiment of the present disclosure and a pneumatic system.
Figure 2:
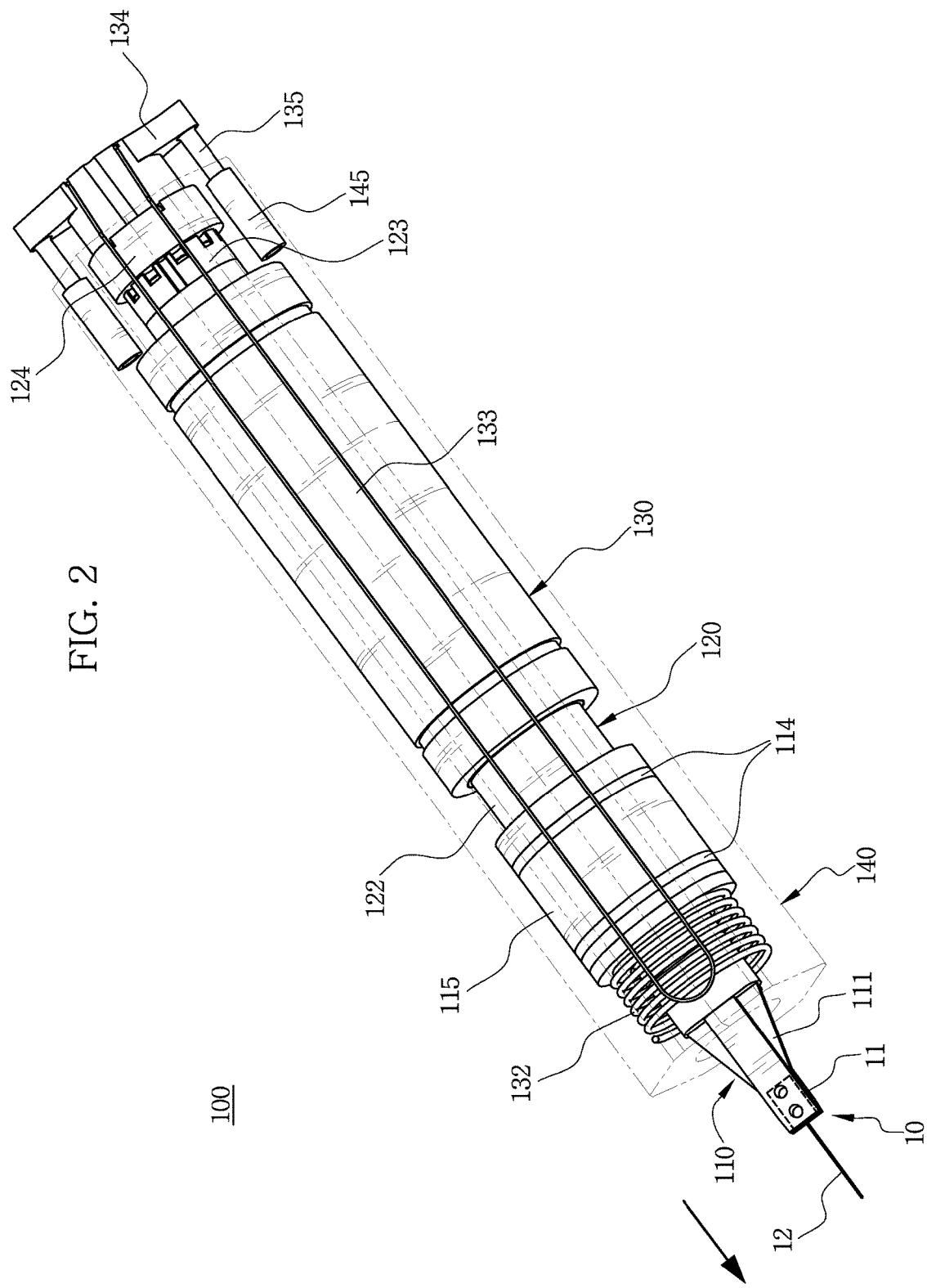
FIG. 2 is a perspective view showing the electrode structure inserting apparatus of FIG. 1.
Figure 3:
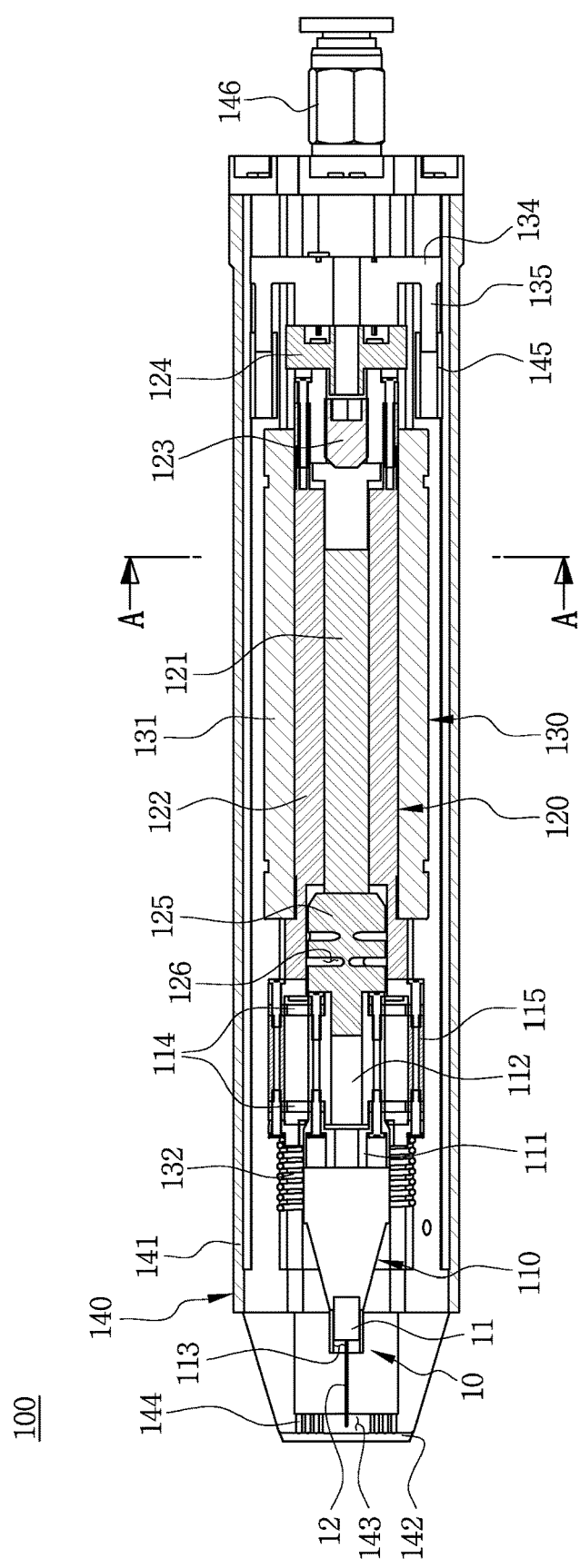
FIG. 3 is a cross-sectional view showing the electrode structure inserting apparatus of FIG. 1.

Referring to FIGS. 1 to 3, an electrode structure inserting apparatus 100 according to an embodiment of the present disclosure includes an electrode structure fixing unit 110, a vibration generator 120, a linear driving unit 130 and a nerve fixing unit 140.

The electrode structure inserting apparatus 100 inserts an electrode structure 10 into a nerve 1 in the biological tissue. The electrode structure 10 may include an electrode 11 and an electrode body 12 to which the electrode 11 is fixed. The electrode structure 10 may be inserted into the nerve so that an end of the electrode 11 penetrates the surface of the nerve 1 and is located in the nerve 1, or the electrode 11 completely penetrates the nerve 1 and a middle portion of the electrode 11 is located inside the nerve 1.

Meanwhile, the electrode structure 10 is exemplarily illustrated and described for clear understanding, and it should be understood that various known invasive electrode structures with a probe shape inserted into the nerve 1 by pressurization may be inserted into the nerve 1 by the electrode structure inserting apparatus 100.

The electrode structure 10 is detachably fixed to the electrode structure fixing unit 110. The electrode structure fixing unit 110 may include a fixing member 111 to which the electrode structure 10 is fixed, and a connection member 112 fixedly coupled to a rear end of the fixing member 111 to receive a force for vibration from the vibration generator 120.

The electrode body 12 is placed in an electrode structure fixing groove 113 formed concavely at the fixing member 111 of the electrode structure fixing unit 110. The electrode structure fixing groove 113 is opened toward an insertion end of the electrode body 12 so that the electrode body 12 may be smoothly separated from the electrode structure fixing unit 110 in an insertion direction (a direction depicted by an arrow in FIG. 2).

The electrode body 12 is not separated from the electrode structure fixing groove 113 in the absence of an external force. However, the electrode body 12 may be fixed to the electrode structure fixing groove 113 with an appropriate strength so that the electrode 11 is capable of being separated from the electrode structure fixing unit 110 by a frictional force generated between the electrode 11 and the nerve 1 when the electrode 11 is inserted into the nerve 1.

The electrode structure fixing unit 110 is connected to an insertion end of the vibration generator 120 and vibrates in the insertion direction. The vibration generator 120 gives a force to vibrate the electrode structure fixing unit 110 forward and backward with respect to the insertion direction. By doing so, the electrode structure fixing unit 110 fixedly disposed in parallel with the vibration generator 120 in the insertion direction receives the force from the vibration generator 120 to vibrate forward and backward.

Figure 4:
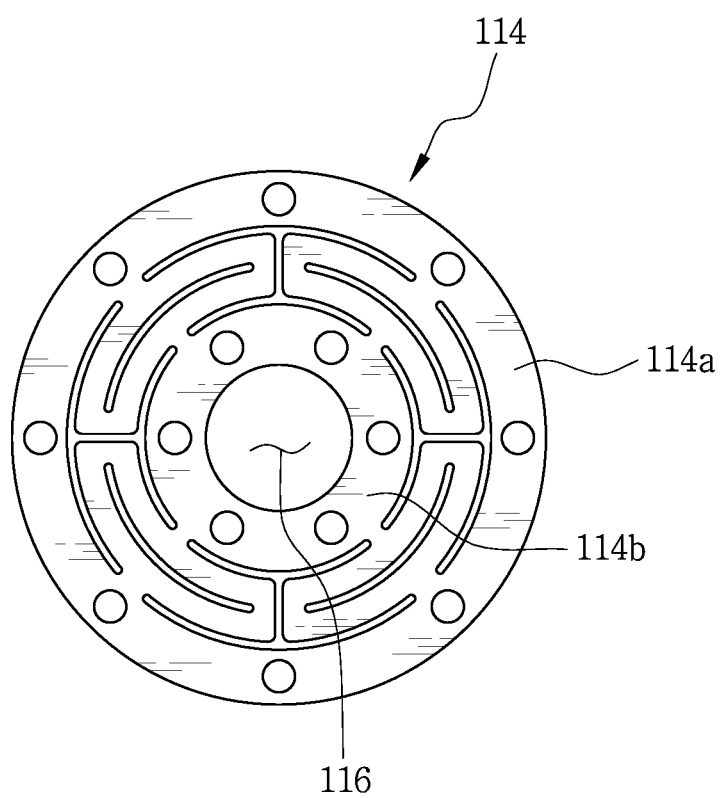
FIG. 4 is a front view showing an elastic plate of the electrode structure inserting apparatus of FIG. 1.

Referring to FIG. 4, the connection member 112 of the electrode structure fixing unit 110 is fixed to an elastic plate 114 which is elastically deformable in the insertion direction, so that the electrode structure fixing unit 110 may vibrate only in the insertion direction and be fixed not to move in a lateral direction of the insertion direction.

The elastic plate 114 is formed to have a thin plate shape made of an elastic material. A through hole 116 is formed at a center of the elastic plate 114, so that the connection member 112 of the electrode structure fixing unit 110 is inserted and fixed therein.

The connection member 112 of the electrode structure fixing unit 110 is fixed to a central portion 114b of the elastic plate 114 by a bolt or the like so as to move due to the elastic characteristic of the elastic plate 114. An edge portion 114a of the elastic plate 114 is fixedly coupled to an alignment cover 115 which is fixedly coupled to a sliding body 122 of the vibration generator 120.

By doing so, even though the connection member 112 of the electrode structure fixing unit 110 is vibrated, the edge portion 114a of the elastic plate 114 may be kept fixed, and only the central portion 114b of the elastic plate 114 may be convexly protruded or concavely recessed in the insertion direction.

If a piezoelectric actuator 121 disposed in the sliding body 122 of the vibration generator 120 is activated to vibrate the electrode structure fixing unit 110, a lateral movement of the electrode structure fixing unit 110 is restricted by the elastic plate 114, and thus the electrode structure fixing unit 110 may vibrate only forwards and backwards with respect to the insertion direction.

By forming the elastic plate 114 to have an appropriate shape, thickness and width as required, it is possible to appropriately adjust the amplitude of vibration, the magnitude of force, the resonance frequency band, or the like of the electrode structure fixing unit 110.

Meanwhile, as shown in the figures, two elastic plates 114 may be arranged in parallel in the insertion direction, and the connection member 112 of the electrode structure fixing unit 110 may pass through the through holes 116 of the respective elastic plates 114 and be fixedly inserted therein at the same time. By doing so, a linear vibration of the electrode structure fixing unit 110 may be ensured more surely. Meanwhile, it is also possible that three or more elastic plates 114 are disposed to guide linear vibration more stably.

The piezoelectric actuator 121 is disposed inside the sliding body 122 and electrically connected to an external power source (not shown). The piezoelectric actuator 121 is expanded and contracted by an inverse piezoelectric effect depending on whether power is supplied or not, thereby generating a force for vibration.

A preload screw 123 for controlling a preload applied to a piezoelectric ceramic is connected to an end of the piezoelectric actuator 121 opposite to the insertion end. Thus, the displacement of vibration or the like caused by the piezoelectric actuator 121 may be controlled.

The end of vibration generator 120 is closed by an inner cap 124. Electric wires connected to the piezoelectric actuator 121 are connected to the external power source through the inner cap 124.

The electrode structure fixing unit 110 and the vibration generator 120 may be connected by a flexible connector 125 which is made of a flexible material. The flexible connector 125 is disposed between the electrode structure fixing unit 110 and the vibration generator 120. By connecting the electrode structure fixing unit 110 and the vibration generator 120 in series, the flexible connector 125 transmits the vibration in the insertion direction, generated from the vibration generator 120, to the electrode structure fixing unit 110.

The flexible connector 125 may be bent in a lateral direction of the insertion direction. In addition, side grooves 126 may be circumferentially formed at a side of the end of the flexible connector 125 to which the vibration generator 120 is connected, so that only a lateral edge portion of the flexible connector 125 may be bent. By doing so, the vibration generated from the piezoelectric actuator 121 in the directions other than the insertion direction is absorbed by the flexible connector 125, and only a component of the vibration in the insertion direction may be transmitted to the electrode structure fixing unit 110.

By doing so, it is possible to prevent a parasitic motion caused by an assembly error and prevent a lateral force from being applied to the piezoelectric ceramic, thereby increasing durability and improving efficiency and controllability.

Figure 9A:
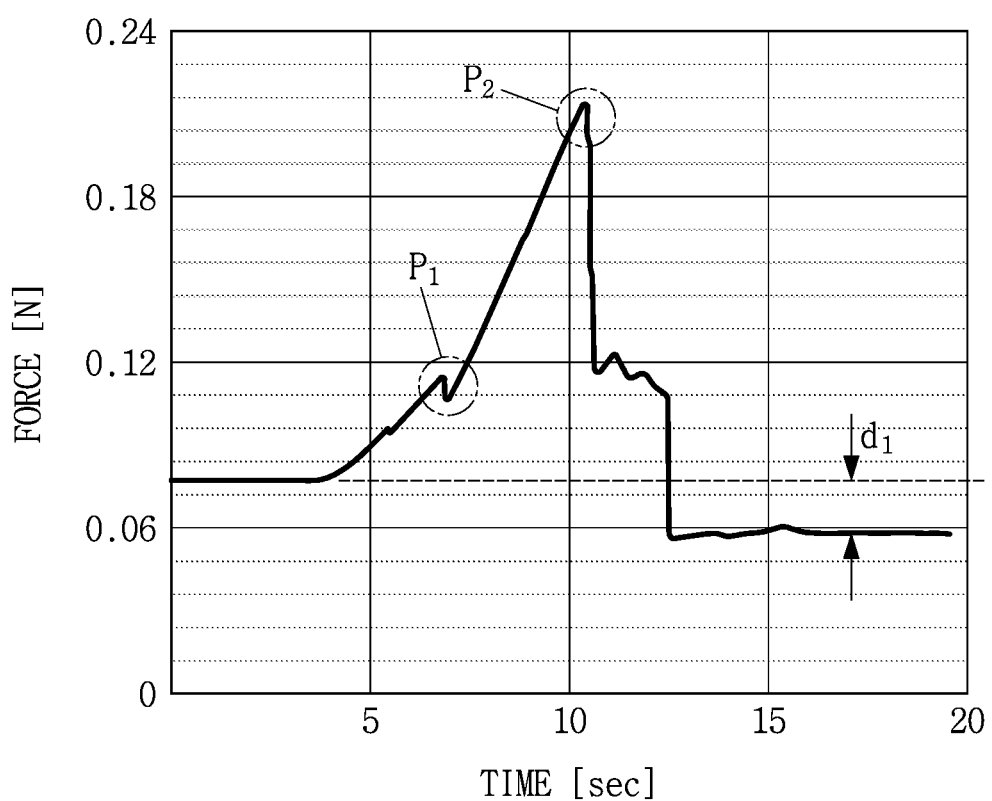
FIGS. 9A and 9B are graphs showing the change of intensity of force demanded to a linear driving unit for the insertion of an electrode structure while the electrode structure is being inserted through a nerve, respectively at a case where vibration is not applied and a case where vibration is applied.
Figure 9B:
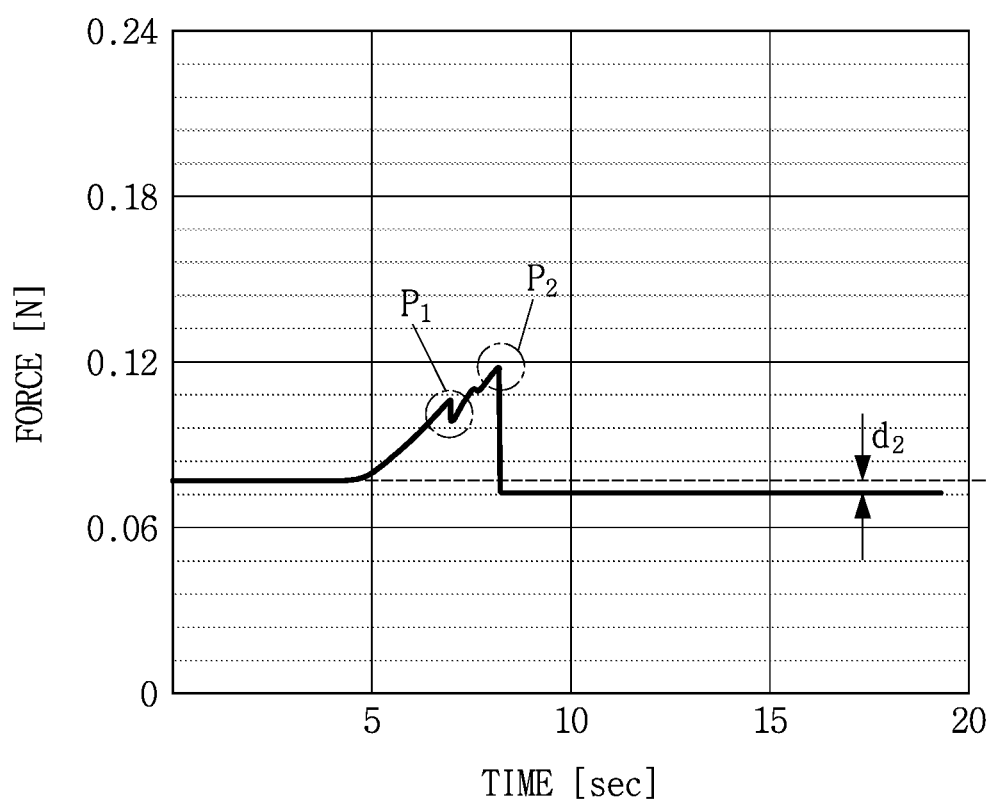

FIGS. 9A and 9B show the magnitude of force required for inserting the electrode structure 10, depending on whether vibration is applied or not, while the electrode 11 is passing through an adjacent membrane of the nerve 1 and a membrane opposite thereto in order.

Referring to FIGS. 9A and 9B, it may be found that the magnitude of force required at a time point $P_1$ when the electrode 11 passes through the adjacent membrane and a time point $P_2$ when the electrode 11 passes through the membrane opposite thereto is greater when vibration is applied, as compared with the case where vibration is not applied.

In addition, as shown in the rear portion of each graph, if vibration is applied, even after the electrode 11 passes the membrane, the nerve 1 is less deformed by the insertion, and thus the force difference $d_2$ required before and after the insertion is very small. However, it may be found that if vibration is not applied, the force difference $d_1$ required before and after the insertion is relatively large as the nerve 1 is deformed after the electrode 11 passes through the membrane.

As described above, by inserting the electrode 11 in the nerve 1 in a vibrating state, it is possible to prevent damage to the nerve and to minimize the deformation of the nerve, so that the nerve is maintained substantially in the same state as before the insertion. Thus, in measuring and analyzing a nerve signal by using the electrode 11, it is possible to obtain more accurate measurement and analysis values.

The electrode structure fixing unit 110 may move in the insertion direction by the linear driving unit 130. The linear driving unit 130 is connected to the electrode structure fixing unit 110 or the vibration generator 120 to move the electrode structure fixing unit 110 and the vibration generator 120 in the insertion direction.

The linear driving unit 130 may include a shape memory alloy wire 133. When a current is applied thereto, the shape memory alloy wire 133 may be contracted to move the vibration generator 120 and the electrode structure fixing unit 110 in the insertion direction.

A front end of the shape memory alloy wire 133 is fixed to an outer body, or a suction body 141 in this embodiment, and a rear end thereof is fixed to a sliding cap 134. The sliding cap 134 may move in the insertion direction since as an insert pole 135 thereof extending in the insertion direction may be inserted into a linear bush 145 or withdrawn from the linear bush 145. The sliding cap 134 is restricted not to move or rotate in a lateral direction.

If the shape memory alloy wire 133 is contracted, as the sliding cap 134 moves forwards, a center protrusion of the sliding cap 134 advances the vibration generator 120 disposed therein. By doing so, the sliding body 122 slides in the insertion direction inside the guide body 131, and the electrode structure fixing unit 110 moves forwards together.

If the shape memory alloy wire 133 is relaxed as the current applied to the shape memory alloy wire 133 is released, the electrode structure fixing unit 110, which has moved in the insertion direction, may return to its original position by receiving a restoration force from the elastic member 132.

As described above, by moving the electrode structure 10 using the contraction and relaxation of the shape memory alloy wire 133 to insert the electrode 11 into the nerve 1, it is possible to control the magnitude of current applied to the shape memory alloy wire 133, the characteristic of the wire, or the like, and thus it is possible to finely control the insertion speed and the magnitude of force. By doing so, the electrode 11 may be moved at an appropriate rate that minimizes deformation of the nerve 1, depending on the quantity, thickness, length, and the like of the electrode 11 inserted into the nerve.

For example, the shape memory alloy wire 133 may be shrunken slowly if a relatively low current is applied slowly to the shape memory alloy wire 133. On the contrary, if a relatively high current is applied for a short time, the shape memory alloy wire 133 may be shrunken rapidly.

The nerve fixing unit 140 includes a suction body 141 in which the electrode structure fixing unit 110 and the vibration generator 120 are disposed. The suction body 141 is formed to have a pen shape as shown in the figure, thereby facilitating easy and convenient use for the user. A hollow is formed inside the suction body 141, and the electrode structure fixing unit 110, the vibration generator 120 and the linear driving unit 130 may be provided in the inner space.

Figure 5:
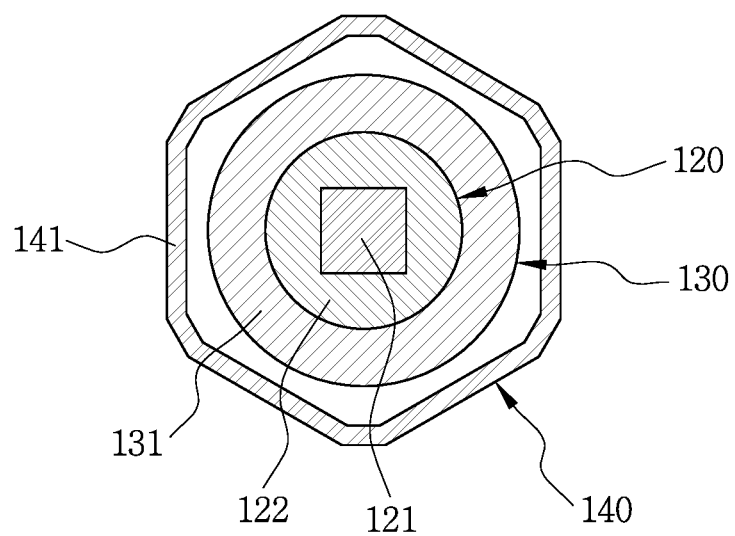
FIG. 5 is a schematic sectional view showing the electrode structure inserting apparatus of FIG. 1, taken along the line A-A of FIG. 3.

As shown in FIG. 5, the sliding body 122, the guide body 131 and the suction body 141 may be aligned so that their central axes are on the same line. The suction body 141 and the guide body 131 may be disposed so that an inner wall of the suction body 141 and an outer wall of the guide body 131 are spaced apart from each other, to form a space in which a negative pressure is maintained by a vacuum pump.

Figure 6:
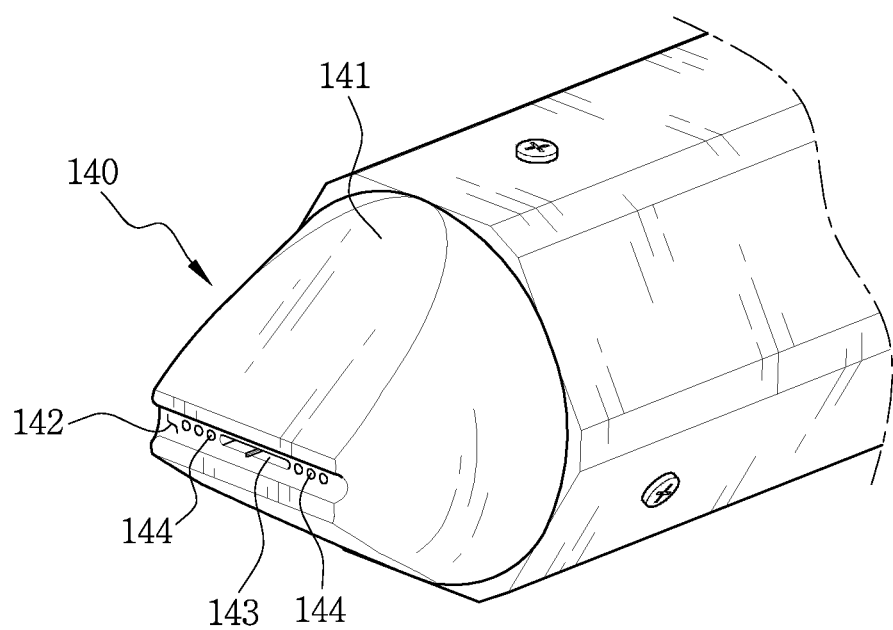
FIG. 6 is a partially enlarged perspective view showing an insertion end of the electrode structure inserting apparatus of FIG. 1.

Referring to FIG. 6, a nerve fixing groove 142 may be formed at the insertion end of the suction body 141 to have a concave shape so that the insertion portion of the nerve 1 into which the electrode structure 10 is to be inserted may be placed therein. An extension length of the nerve fixing groove 142 may be suitably selected so that the nerve 1 having a sufficient length may be placed in the nerve fixing groove 142.

The suction body 141 has an electrode structure discharge hole 143 through which the electrode structure 10 passes, and a suction hole 144 disposed around the electrode structure discharge hole 143 to suck the insertion portion of the nerve 1 therein.

The electrode structure discharge hole 143 is disposed in front of the electrode structure fixing unit 110 and is formed inside the nerve fixing groove 142. If the nerve 1 is placed in the nerve fixing groove 142, the electrode 11 and the nerve 1 are aligned to allow insertion.

One or more suction holes 144 may be formed around the electrode structure discharge hole 143 to transfer the negative pressure inside the suction body 141 to the nerve 1 placed in the nerve fixing groove 142, thereby stably fixing the nerve 1.

Figure 7:
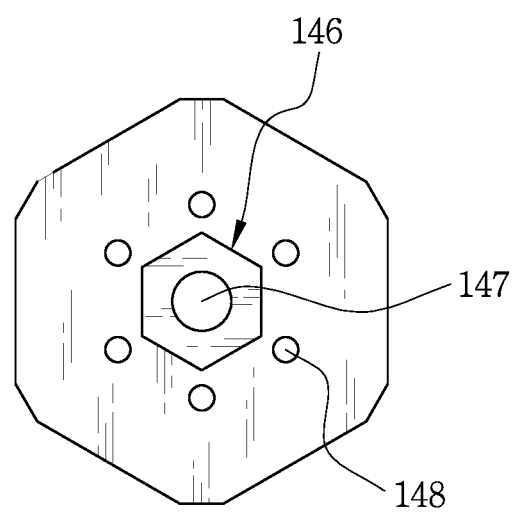
FIG. 7 is a rear view showing the electrode structure inserting apparatus of FIG. 1.

Referring to FIG. 7, a pneumatic pipe connection unit 146 is disposed at a rear end of the suction body 141. A pneumatic pipe 20 is connected to the inside of the suction body 141 through a pipe hole 147 formed at the rear end of the suction body 141 to allow fluid communication.

Referring to FIG. 1, the pneumatic pipe 20 coming from the suction body 141 may be connected to a filter 200 for filtering out foreign matters, moisture and the like, a solenoid valve 300 for controlling the flow rate, a regulator 400 for adjusting the pressure to an appropriate level, a vacuum pump 500 for sucking in the air from the suction body 141, and the like.

By doing so, a negative pressure may be formed in the suction body 141 as the air is sucked from the suction body 141 through the pneumatic pipe 20 by the operation of the vacuum pump 500.

Meanwhile, electric wires connected to the piezoelectric actuator 121 and the shape memory alloy wire 133 pass through a cable hole 148 formed at the rear end of the suction body 141 and connected to the external power source. The pipe hole 147 and the cable hole 148 may be tightly sealed so that no gap is created to maintain the negative pressure inside the suction body 141 when the electric wires and the pipe are connected.

Meanwhile, a camera (not shown) may be mounted at an outer side surface of the suction body 141. When the electrode structure 10 is inserted, the insertion portion of the nerve 1 may be photographed as an enlarged view to assist in precise insertion operation. A lighting device (not shown) may be provided together with the camera to increase the visibility of the insertion portion of nerve 1.

Hereinafter, an exemplary method of using the electrode structure inserting apparatus 100 will be described.

Figure 8:
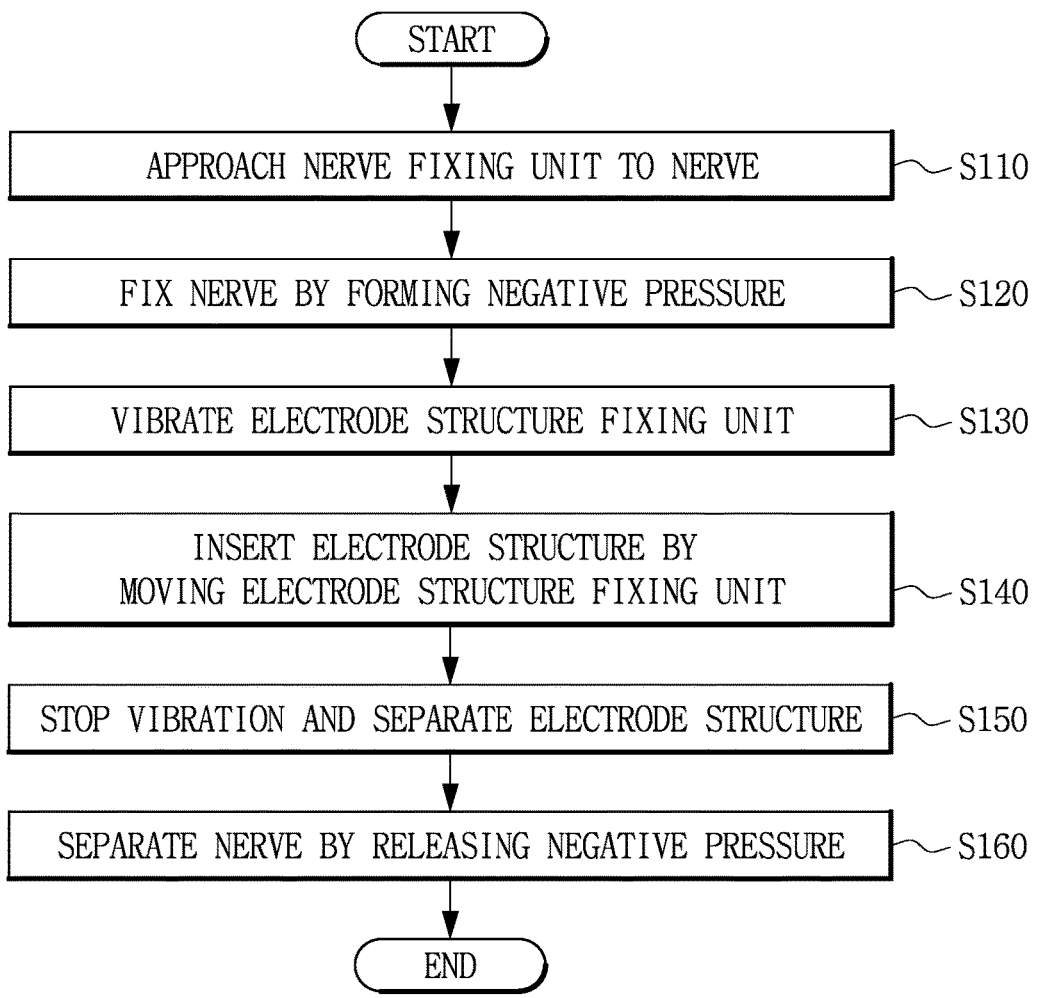
FIG. 8 is a flowchart for illustrating each step of an exemplarily method for using the electrode structure inserting apparatus of FIG. 1.

Referring to FIG. 8, an exemplary method of using the electrode structure inserting apparatus 100 includes the steps of: approaching the nerve fixing unit 140 to the nerve 1 (S110), fixing the nerve 1 by forming a negative pressure in the suction body 141 (S120), applying a voltage to the piezoelectric actuator 121 to vibrate the electrode structure fixing unit 110 (S130), inserting the electrode structure 10 into the nerve 1 by moving the electrode structure fixing unit 110 in the insertion direction by means of the linear driving unit 130 (S140), stopping the vibration and separating the electrode structure 10 from the electrode structure fixing unit 110 (S150), and releasing the negative pressure and separating the nerve 1 (S160).

First, the nerve fixing unit 140 is approached to the nerve 1 so that the nerve fixing groove 142 of the nerve fixing unit 140 and the insertion portion of the nerve 1 into which the electrode 11 is to be inserted are aligned close to each other (S110). The nerve 1 in the biological tissue is exposed to the outside, and the nerve is disposed so that a portion of the protruding nerve 1 into which the electrode 11 is to be inserted is located in front of the electrode structure discharge hole 143, and the nerve 1 is inserted into the nerve fixing groove 142.

Next, the vacuum pump is operated to form a negative pressure in the suction body 141 to fix the nerve 1 (S120). As the negative pressure is formed in the suction body 141, the nerve 1 may be closely adhered and fixed to the inner wall of the nerve fixing groove 142 by means of the electrode structure discharge hole 143 and the suction hole 144. The negative pressure is continuously maintained during the insertion operation, so that the nerve 1 may be stably placed without moving at a fixed position.

Next, a voltage is applied to the piezoelectric actuator 121 from the external power source to vibrate the electrode structure fixing unit 110 (S130). The vibration caused by the piezoelectric actuator 121 is transmitted to the electrode structure fixing unit 110 as a vibration component in the insertion direction by the flexible connector 125 and the elastic plate 114. The vibration continues until the electrode 11 is fully inserted into the nerve 1, and the amplitude, frequency or the like of the vibration may be appropriately adjusted at each step as needed.

Next, the shape memory alloy wire 133 is contracted to move the vibration generator 120 and the electrode structure fixing unit 110 forwards in the insertion direction so that the electrode 11 of the electrode structure 10 is inserted into the nerve 1 (S140).

The moving speed of the electrode structure fixing unit 110 may be appropriately adjusted in consideration of the quantity of the electrode 11 to be inserted into the nerve 1, the thickness of the electrode 11, and the epineurium state of the nerve 1. For example, when a plurality of electrode arrays are inserted into the nerve 1, the electrode structure fixing unit 110 may be moved relatively rapidly. When only one electrode is inserted, the electrode structure fixing unit 110 may be moved relatively slowly.

Next, the vibration is stopped, and the shape memory alloy wire 133 is relaxed so that the electrode structure fixing unit 110 retreats by the restoring force of the elastic member 132 to separate the electrode structure 10 from the electrode structure fixing unit 110 (S150). At this time, the electrode structure fixing unit 110 may retreat at a proper speed so that the electrode structure 10 is not separated again from the nerve 1 in the retreat process.

Finally, the negative pressure in the suction body 141 is released, and the nerve is separated from the nerve fixing groove 142 (S160). It should be noted that the nerve 1 should be carefully separated in order to prevent the nerve 1 from being deformed or damaged during the separation of the nerve 1.

If the electrode structure inserting apparatus 100 according to an embodiment of the present disclosure as described above is used, it is possible to reduce the force required to insert the electrode 11 into the nerve through the epineurium while vibrating the electrode structure 10, and thus it is possible to reduce the deformation and damage of the nerve caused by the insertion of the electrode 11 and to prevent the electrode 11 from being bent during the insertion.

In addition, since the shape memory alloy wire 133 is electrically controlled, it is possible to further reduce the deformation and damage of the nerve by precisely controlling the speed and intensity at which the electrode structure 10 is inserted into the nerve.

Moreover, since the electrode fixing unit 110, the vibration generator 120 and the linear driving unit 130 are included in the suction body 141, the electrode structure inserting apparatus 100 may have a smaller size. Due to the smaller size, a user may grip the electrode structure 10 and insert the electrode structure 10 by a simple motion, thereby ensuring ease and versatility of the inserting motion. It would be also possible to more precisely insert the electrode by additionally providing a device for correcting micro tremors of the hand.

[Reference Signs]

| | |
|---|---|
| 110: electrode structure fixing unit | 111: fixing member |
| 112: connection member | 113: electrode structure fixing groove |
| 114: elastic plate | 115: alignment cover |
| 116: through hole | 120: vibration generator |
| 121: piezoelectric actuator | 122: sliding body |
| 123: preload screw | 124: inner cap |
| 125: flexible connector | 126: side groove |
| 130: linear driving unit | 131: guide body |
| 132: elastic member | 133: shape memory alloy wire |
| 134: sliding cap | 135: insert pole |
| 140: nerve fixing unit | 141: suction body |
| 142: nerve fixing groove | 143: electrode structure discharge hole |
| 144: suction hole | 145: linear bush |
| 146: pneumatic pipe connection unit | 147: pipe hole |
| 148: cable hole | 1: nerve |
| 10: electrode structure | 11: electrode |
| 12: electrode body | 20: pneumatic pipe |
| 100: electrode structure inserting apparatus | 200: filter |
| 300: solenoid valve | 400: regulator |
| 500: vacuum pump | |

What is claimed is:

1. An electrode structure inserting apparatus for inserting an invasive electrode structure into a nerve in a biological tissue, the apparatus comprising:
    a housing, the housing having a first end, a second end and a longitudinal axis extending between the first end and the second end;
    an electrode structure support at the first end of the housing, the electrode structure detachably fixed to the electrode structure support;
    a vibration generator in the housing and spaced from the electrode structure support along the longitudinal axis, the vibration generator connected to the electrode structure support to vibrate the electrode structure support in an insertion direction of the electrode structure; and
    a suction body attached to the first end of the housing, the suction body having a discharge hole for allowing passage of the electrode structure and a suction hole.

2. The electrode structure inserting apparatus according to claim 1, further comprising:
    a linear driving unit configured to move the electrode structure support in the insertion direction.

3. The electrode structure inserting apparatus according to claim 1, further comprising:
    a flexible connector disposed between the electrode structure support and the vibration generator to connect the electrode structure support and the vibration generator.

4. The electrode structure inserting apparatus according to claim 3, wherein the flexible connector has a side groove circumferentially formed at a side of an end thereof to which the vibration generator is connected.

5. The electrode structure inserting apparatus according to claim 1, further comprising:
    an elastic plate having a through hole in which the electrode structure support is inserted and fixed, the elastic plate being elastically deformable in the insertion direction.

6. The electrode structure inserting apparatus according to claim 5, wherein two or more elastic plates are arranged in parallel in the insertion direction.

7. The electrode structure inserting apparatus according to claim 1, wherein the vibration generator includes a piezoelectric actuator.

8. The electrode structure inserting apparatus according to claim 2, further comprising:
    an elastic member configured to apply a restoration force to the electrode structure support which is moved in the insertion direction.

9. The electrode structure inserting apparatus according to claim 2, further comprising:
    a guide body to which the vibration generator is connected to be slidable in the insertion direction.

10. The electrode structure inserting apparatus according to claim 1, wherein the suction body has a nerve fixing groove formed concavely so that the insertion portion of the nerve is placed therein, and
    wherein the discharge hole and suction hole are in the nerve fixing groove.

11. The electrode structure inserting apparatus according to claim 1, further comprising a vacuum generator connected to the housing.

12. An electrode structure inserting apparatus for inserting an invasive electrode structure into a nerve in a biological tissue, the apparatus comprising:
    an electrode structure support to which the electrode structure is detachably fixed;
    a vibration generator connected to the electrode structure support to vibrate the electrode structure support in an insertion direction of the electrode structure; and
    a linear driving unit configured to move the electrode structure support in the insertion direction,
    wherein the linear driving unit includes a shape memory alloy wire for moving the electrode structure support in the insertion direction.

13. An electrode structure inserting apparatus for inserting an invasive electrode structure into a nerve in a biological tissue, the apparatus comprising:
    a housing, the housing having a first end, a second end and a longitudinal axis extending between the first end and the second end;
    an electrode structure support at the first end of the housing to which the electrode structure is detachably fixed;
    a vibration generator in the housing and spaced from the electrode structure support along the longitudinal axis, the vibration generator connected to the electrode structure support to vibrate the electrode structure support in an insertion direction of the electrode structure,
    wherein the vibration generator comprises a piezoelectric actuator and a sliding body coaxial with the piezoelectric actuator.

14. The electrode structure inserting apparatus according to claim 13, further comprising an elastic member between the electrode structure support and the vibration generator.

* * * * *